United States Patent [19]

Kohayakawa

[11] Patent Number: 5,506,632
[45] Date of Patent: Apr. 9, 1996

[54] OPHTHALMOLOGIC APPARATUS HAVING AN ELECTRICAL MAGNIFIER

[75] Inventor: Yoshimi Kohayakawa, Yokohama, Japan

[73] Assignee: Canon Kabushiki Kaisha, Tokyo, Japan

[21] Appl. No.: 363,008

[22] Filed: Dec. 23, 1994

[30] Foreign Application Priority Data

Dec. 30, 1993 [JP] Japan ................... 5-351810

[51] Int. Cl.⁶ ........................................ A61B 3/10
[52] U.S. Cl. .................... 351/205; 351/206; 354/62
[58] Field of Search ................................ 351/200, 205, 351/206, 208, 210, 221; 354/62

[56] References Cited

U.S. PATENT DOCUMENTS

| | | | |
|---|---|---|---|
| 4,820,037 | 4/1989 | Kohayakawa et al. | 351/211 |
| 5,037,194 | 8/1991 | Kohayakawa et al. | 351/224 |
| 5,144,346 | 9/1992 | Nakamura et al. | 351/208 |
| 5,280,313 | 1/1994 | Kohayakawa | 351/211 |
| 5,287,129 | 2/1994 | Sano et al. | 351/206 |

*Primary Examiner*—Anita Pellman Gross
*Assistant Examiner*—Huy Mai
*Attorney, Agent, or Firm*—Fitzpatrick, Cella, Harper & Scinto

[57] ABSTRACT

An ophthalmologic apparatus has a main body for effecting an eye examination, a television camera for picking up the image of an eye to be examined, a television monitor for displaying the image of the eye to be examined picked up by the television camera, and an electrical magnifier for electronically magnifying the image of the eye to be examined displayed on the television monitor.

10 Claims, 3 Drawing Sheets

5,506,632

OPHTHALMOLOGIC APPARATUS HAVING AN ELECTRICAL MAGNIFIER

BACKGROUND OF THE INVENTION

1. Field of the Invention

This invention relates to an ophthalmologic apparatus for use in an ophthalmic clinic or the like.

2. Related Background Art

With an eye examining apparatus according to the prior art, an examiner effects the alignment of the apparatus with an eye to be examined while observing the image of the eye to be examined by means of a television monitor.

When effecting this alignment, the examiner selects a low magnification at first and observes the image of the eye to be examined in a wide field of view, and then effects the alignment to some degree. Thereafter, the examiner selects a high magnification and enlarges the image of the eye to be examined, and then must effect the alignment precisely.

In the eye examining apparatus according to the prior art, however, the display magnification of the monitor is fixed and the image of the eye to be examined cannot be observed on an enlarged scale and therefore, there occurs an inconvenience. Also, the observation optical system of the apparatus does not have a focal-length changing function and therefore, the range of the image of the eye to be examined recorded on film or the like cannot be displayed on the television monitor, and this is inconvenient.

SUMMARY OF THE INVENTION

It is a first object of the present invention to solve the above-noted problems and to provide an ophthalmologic apparatus which can be easily and accurately aligned with an eye to be examined and enables the photographing range to be displayed correctly without the focal-length changing function of an observation optical system.

Other objects of the present invention will become apparent from the following detailed description of some embodiments of the invention.

DESCRIPTION OF THE PREFERRED EMBODIMENTS

Figure 1:
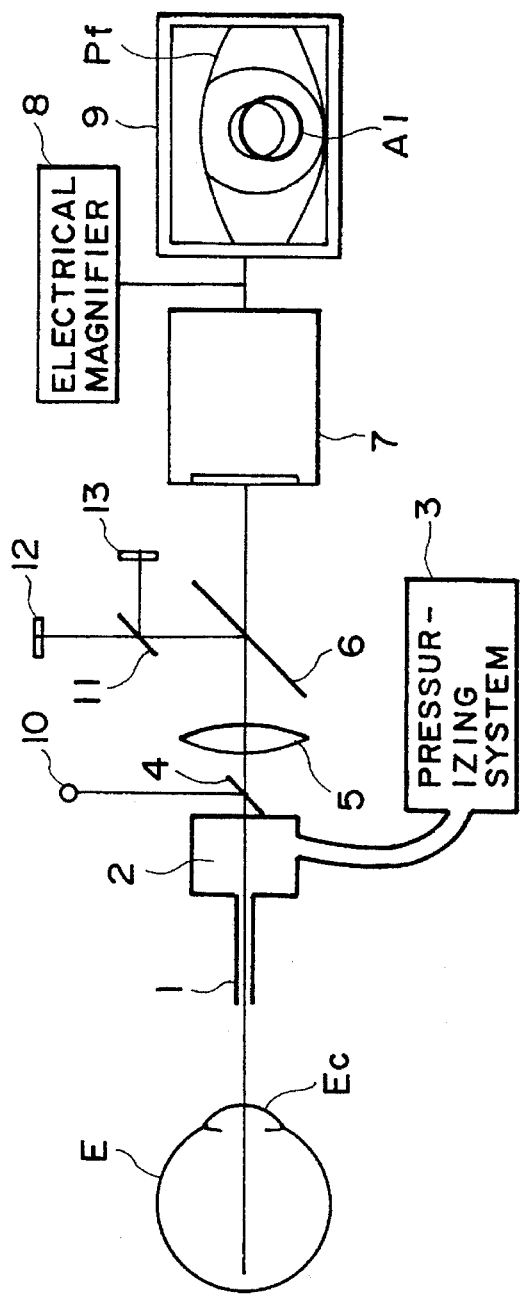
FIG. 1 shows the construction of a first embodiment of the present invention.

The invention will hereinafter be described in detail with respect to some embodiments thereof shown in the drawings.

FIG. 1 shows the construction of a first embodiment applied to an eye pressure meter. A nozzle 1 opposed to an eye E to be examined is provided so as to protrude from a chamber 2 which is connected to a pressuring system 3. A beam splitter 4, a lens 5, a dichroic mirror 6 and a television camera 7 are disposed on an optical path behind the chamber 2, and the output of the television camera 7 is connected to an electrical magnifier 8 and to a television monitor 9. A light source 10 for measurement is disposed on an optical path in the direction of incidence of the beam splitter 4, a beam splitter 11 and a photodiode 12 are disposed on an optical path in the direction of reflection of the dichroic mirror 6, and a photodiode 13 is disposed on an optical path in the direction of reflection of the beam splitter 11.

A beam of light from the light source 10 for measurement is reflected by the beam splitter 4, passes through the chamber 2 and the interior of the nozzle 1 and irradiates the cornea Ec of the eye E to be examined. The reflected beam of light then returns along the same optical path, passes through the beam splitter 4 and the lens 5, is reflected by the dichroic mirror 6 and the beam splitter 11 and is received by the photodiode 13.

When alignment is to be effected, the reflected beam of light on the front eye part of the eye E to be examined by the illuminating light passes through the chamber 2, the beam splitter 4, the lens 5 and the dichroic mirror 6, is picked up as a front eye part image Pf by the television camera 7, and is displayed on the television monitor 9 with an electronically produced alignment mark A1.

An examiner roughly adjusts the position of the apparatus so that the pupil of the eye to be examined may become concentric with the alignment mark A1 while observing the television monitor 9. When the alignment is done to some degree, the cornea-reflected light from the light source 10 for measurement arrives at the photodiode 13, and the received light signal in the photodiode 13 is introduced into the electrical magnifier 8.

When the received light signal of the photodiode 13 is introduced into the electrical magnifier 8, the electrical magnifier 8 once records the video signal of the central portion of the image pickup screen of the television camera 7 into an internal memory, and thereafter digitally magnifies this image, and a front eye part image Pf', more magnified than the front eye part image Pf, as shown in FIG. 2 is again displayed as a video signal on the television monitor 9. Further, the alignment mark A1 is likewise magnified and displayed as an alignment mark A2 on the television monitor 9. This image processing needs the time of about one image field, but poses no problem to the alignment because the display of moving images is possible.

Figure 2:
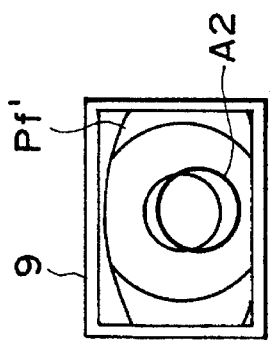
FIG. 2 is an illustration of the image of the front eye part of an eye displayed on a television monitor during enlargement observation.

The examiner effects fine adjustment so that the magnified pupil portion may become concentric with the alignment mark A2 while observing the television monitor 9 as shown in FIG. 2. Thereupon, the photodiode 13 becomes conjugate with the cornea Ec of the eye E to be examined, and the focusing of the cornea-reflected beam of light on the photodiode 13 is done.

When the photodiode 13 detects a quantity of light equal to or greater than a reference value, it outputs a detection signal to the pressuring system 3. The pressuring system 3 compresses air, and this compressed air is sent to the chamber 2, passes through the nozzle 1 and is blown against the eye E to be examined, thereby deforming the cornea Ec. When the cornea Ec of the eye E to be examined is deformed into a predetermined shape, the photodiode 12 becomes conjugate with the cornea Ec, and the cornea-reflected image by the light source 10 for measurement is formed on the photodiode 12. The pressure value of the chamber at this time is converted into the eye pressure value of the eye E to be examined.

In this embodiment, the display magnification of the television monitor 9 is automatically changed over on the basis of the detection signal of the photodiode 13, but alternatively, a switch capable of selecting the display magnification arbitrarily may be provided discretely.

In the present embodiment, when the alignment is not complete, the front eye part can be observed in a wide field of view, and when the alignment becomes complete to some degree, the front eye part image can be changed over to a magnified image and observed and therefore, more accurate alignment can be accomplished.

Figure 3:
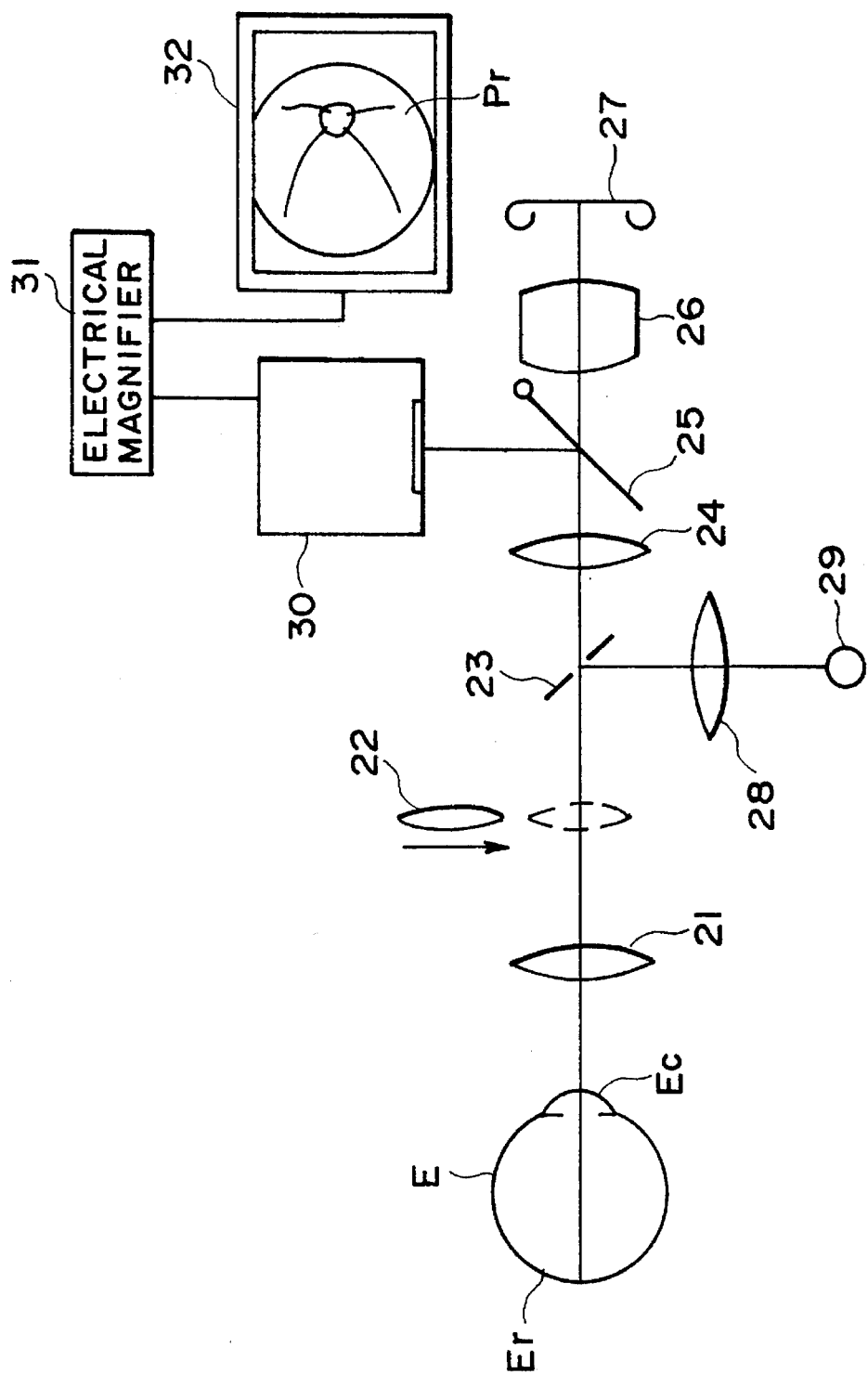
FIG. 3 shows the construction of a second embodiment of the present invention.

Referring now to FIG. 3 which shows the construction of a second embodiment of the present invention applied to a retinal camera, on an optical path behind an objective lens 21 opposed to an eye E to be examined, there are disposed a lens 22 retractable from the optical path, an apertured mirror 23 which is in a conjugate relationship with the pupil of the eye to be examined, a lens 24, a quick return mirror 25, a variable power lens 26 and film 27, and a lens 28 and a light source 29 for illuminating the fundus of the eye which are disposed in the direction of incidence of the apertured mirror 23. A television camera 30 is disposed on an optical path in the direction of reflection of the quick return mirror 25, and the output of the television camera 30 is connected to an electrical magnifier 31 and a television monitor 32.

During the observation of the image of the fundus of the eye, the lens 22 is retracted from the optical path. A beam of light from the light source 29 for illuminating the fundus of the eye passes through the lens 28, the apertured mirror 23 and the objective lens 21 and illuminates the fundus Er of the eye E to be examined. The reflected beam of light from the fundus Er of the eye returns along the same optical path, passes through the opening portion of the apertured mirror 23 and the lens 24, is reflected by the quick return mirror 25, and is received as an eye fundus image by the television camera 30, and the eye fundus image Pr is displayed on the television monitor 32. The examiner adjusts the photographing magnification by the variable power lens 26 while observing the television monitor 32.

Figure 4:
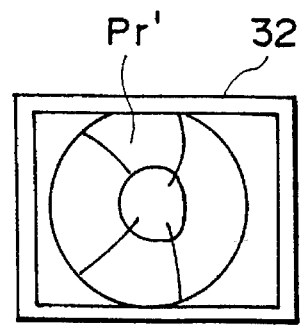
FIG. 4 is an illustration of the image of the fundus of the eye displayed on the television monitor during enlargement observation.

During photographing, the variable power lens 26 and the electrical magnifier 31 are operatively associated with each other, and when the magnification of the variable power lens 26 is made great by an adjusting knob, not shown, the electrical magnifier 31 introduces a video signal from the television camera thereinto and carries out the magnifying process, and the video signal is displayed as a magnified eye fundus image Pr' on the television monitor 32 as shown in FIG. 4. The observation field of the television monitor 32 at this time is the same as the range within which the eye fundus image is recorded on the film 27. The examiner selects a region to be recorded while observing the television monitor 32.

During photographing, the quick return mirror 25 is jumped up and the magnified eye fundus image Pr' is recorded on the film 27.

Figure 5:
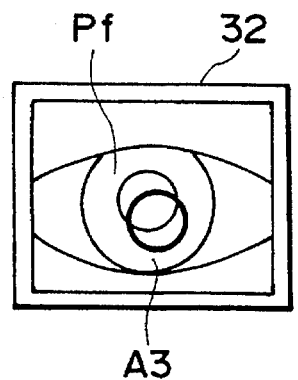
FIG. 5 is an illustration of the image of the front eye part of the eye displayed on the television monitor.

During the observation of the front eye part, the lens 22 is inserted into the optical path. The reflected beam of light from the front eye part of the eye E to be examined passes through the objective lens 21, the lens 22, the apertured mirror 23 and the lens 24, is reflected by the quick return mirror 25, is received as a front eye part image Pf by the television camera 30, and is displayed on the television monitor 32 with an alignment mark A3, as shown in FIG. 5. The examiner effects rough alignment so that the pupil of the eye to be examined may become concentric with the alignment mark A3 while observing the television monitor 32.

Figure 6:
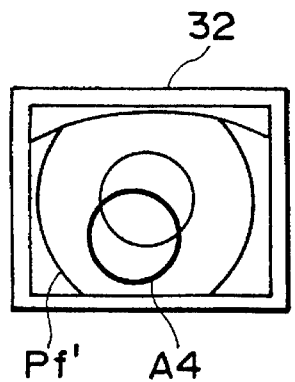
FIG. 6 is an illustration of the image of the front eye part of the eye displayed on the television monitor.

Thereafter, the examiner adjusts the magnification of the variable power lens 26 to the magnified side for the purpose of fine adjustment. The examiner operates the electrical magnifier 31, introduces the video signal of the television camera 30 thereinto and electronically magnifies the front eye part image Pf and the alignment mark A3. The front eye part image Pf and the alignment mark A3 are displayed as a magnified front eye part image Pf' and an alignment mark A4, respectively, on the television monitor 32, as shown in FIG. 6. The examiner effects fine adjustment so that the pupil portion of the front eye part image Pg may become concentric with the alignment mark A4 while observing the television monitor 32.

In the present embodiment, even when only the photographing system is accompanied by a variable power lens, observation can be done in the same field of view as the photographing system. And further, easy alignment with a wide field and fine alignment with a magnified image are possible.

What is claimed is:

1. An ophthalmologic apparatus comprising:

a main body for effecting an eye examination;

image pickup means for picking up an image of an eye to be examined;

display means for displaying the image of the eye to be examined picked up by said image pickup means; and electrical magnifying means for electronically magnifying the image of the eye to be examined displayed on said display means.

2. The apparatus according to claim 1, wherein said main body effects the measurement of the eye pressure of the eye to be examined.

3. The apparatus according to claim 1, further comprising detecting means for detecting an alignment state and wherein said electrical magnifying means is operated on the basis of the output from said detecting means.

4. The apparatus according to claim 1, wherein said electrical magnifying means comprises memory means for once storing a video signal of the eye to be examined picked up by said image pickup means, and means for digitally magnifying the video signal relative to the image stored in said memory means.

5. The apparatus according to claim 1, wherein said display means displays a mark for alignment simultaneously with the image of the eye to be examined.

6. The apparatus according to claim 1, wherein said main body effects the photographing of the fundus of the eye to be examined.

7. The apparatus according to claim 6, wherein said electrical magnifying means is responsive to the enlargement of the projection magnification of said main body to electronically magnify the image of the eye to be examined.

8. An ophthalmologic apparatus comprising:

a main body for effecting an eye examination;

image pickup means for picking up the image of an eye to be examined;

display means for displaying the image of the eye to be examined picked up by said image pickup means; and electrical magnification changing means for electronically changing the magnification of the image of the eye to be examined displayed on said display means.

9. The apparatus according to claim 8, wherein said electrical magnification changing means has memory means for once storing a video signal of the eye to be examined picked up by said image pickup means, and means for effecting a magnification changing process relative to the video signal stored in said memory means.

10. The apparatus according to claim 8, wherein said display means displays a mark for alignment simultaneously with the image of the eye to be examined.

* * * * *